US005919480A

United States Patent [19]
Kedar et al.

[11] Patent Number: 5,919,480
[45] Date of Patent: Jul. 6, 1999

[54] LIPOSOMAL INFLUENZA VACCINE COMPOSITION AND METHOD

[75] Inventors: Eliezer Kedar, Jerusalem; Ilan Babai, Petach Tivka; Yechezkel Barenholz, Jerusalem, all of Israel

[73] Assignee: Yissum Research Development Company of the Hebrew University of Jerusalem, Jerusalem, Israel

[21] Appl. No.: 08/880,238

[22] Filed: Jun. 23, 1997

Related U.S. Application Data

[60] Provisional application No. 60/020,063, Jun. 24, 1996.

[51] Int. Cl.[6] ................................................. A61K 9/127
[52] U.S. Cl. ...................... 424/450; 424/206.1; 436/829
[58] Field of Search ............................... 424/450, 206.1; 436/829

[56] References Cited

U.S. PATENT DOCUMENTS

| | | | |
|---|---|---|---|
| 4,117,113 | 9/1978 | Allison | 424/89 |
| 4,235,877 | 11/1980 | Fullerton | 424/89 |
| 5,679,356 | 10/1997 | Bonnem | 424/278.1 |

OTHER PUBLICATIONS

Ben–Ahmeida, E.T.S. et al., "IgG Subclass Response and Protection Against Challenge Following Immunisation of Mice with Various Influenza A Vaccines," *Med. Microbiol.* 40:261–269 (1994).

Glück, R. et al., "Immunogenicity of New Virosome Influenza Vaccine in Elderly People," *The Lancet.* 344;160–163 (1994).

Gregoriadis, G. et al., "Liposomes Enhance the Immunogenicity of Reconstituted Influenza Virus A/PR/8 Envelopes and the Formation of Protective Antibody by Influenza Virus A/Sichuan/87 (H3N2) Surface Antigen," *Vaccine.* 10:(11) 747–753 (1992).

Kedar, E. et al, "Delivery of Cytokines by Liposomes. I. Preparation and Characterization of Interleukin–2 Encapsulated in Long–Circulating Sterically Stabilized Liposomes," *Journal of Immunotherapy.* 16:(1) 47–59 (1994).

Mbawuike, I.N. et al., "Enhancement of the Protective Efficacy of Inactivated Influenza A Virus Vaccine in Aged Mice by IL–2Liposomes," *Vaccine.* 8:347–352 (1990).

Iinuma, H. et al., "Characteristics of Cytotoxic T Lymphocytes Directed to Influenza Virus Haemagglutinin Elicited by Immunization with Muramyldipeptide–Influenza Liposome Vaccine," *Scand. J. Immunol.* 41:1–10 (1995).

Powers, D.C. et al., "Cytotoxic T Lymphocyte Responses to a Liposome–Adjuvanted Influenza A Virus Vaccine in the Elderly," *The Journal of Infectious Diseases.* 172:1103–1107 (1995).

Tan, Biochemical Soc. Transmitting 17 (14) p. 693, 1989.

*Primary Examiner*—Gollamudi S. Kishore
*Attorney, Agent, or Firm*—LeeAnn Gorthey

[57] ABSTRACT

Subunit influenza vaccines containing an influenza H/N antigen and a cytokine immunopotentiator, where at least one and preferably both are encapsulated in liposomes, are described. The vaccines stimulate a strong humoral and CTL response. Also described are methods of immunization using such vaccines.

20 Claims, 10 Drawing Sheets

LIPOSOMAL INFLUENZA VACCINE COMPOSITION AND METHOD

This application claims the priority of U.S. Provisional Application Ser. No. 60/020,063 filed Jun. 24, 1996, which is incorporated herein by reference.

FIELD OF THE INVENTION

The present invention relates to subunit influenza vaccine compositions in which an antigen and a cytokine immunopotentiator are encapsulated in liposomes, and to methods of immunization using such compositions.

References

Adler, A. et al., *Cancer Biotherapy* 10:293–306 (1995).
Arnon, R. et al., *Curr. Opin. Immunol.* 4:449–453 (1992).
Arnon, R. et al., *FASEB J.* 6:3265–3274 (1992).
Ben-Ahmeida, E. T. S. et al., *Antiviral Res.* 21:217–231 (1993).
Both, G. W. et al., *J. Virol.* 48:52–60 (1983).
Engelhard, D. et al., *Bone Marrow Transp.* 11:1–5 (1993).
Gazit, E. et al., *Cancer Immunol. Immunother.* 38:243–52 (1994).
Gillis, S. et al., *J. Immunol.* 120:2027–2031 (1978).
Harlow, E. and Lane, D., (eds.), *ANTIBODIES: A LABORATORY MANUAL*, Cold Spring Harbor Laboratory, New York, 1988, p. 99.
Kedar, I. et al., *J. Immunotherapy* 16:47–59 (1994).
Minamide, L. S. et al., *Anal. Biochem.* 190:66–70 (1990).
Mossmann, T., *J. Immunol. Meth.* 65:55–63 (1983).
Potter, C. W., in *BASIC AND APPLIED INFLUENZA RESEARCH*, Beare, A. S. (Ed.), CRC Press, Florida, 1982, pp. 119–204.
Sears, B. D., U.S. Pat. No. 4,426,330 (January 1984).
Sears, B. D., U.S. Pat. No. 4,534,899 (August 1985).
Shapira-Nahor, O. and Zakay-Rones, Z., *J. Med. Virol.* 15:81–89 (1985).
Szoka, F., Jr. et al., U.S. Pat. No. 4,235,871 (1980).
Szoka, F., Jr. et al., *Ann. Re. Biophys. Bioeng.* 9:467 (1980).
Woodle, M. C. et al., U.S. Pat. No. 5,013,556 (1991).

BACKGROUND OF THE INVENTION

The highly contagious influenza virus is the major contributor to acute respiratory infections. Conventional influenza vaccines contain inactivated microorganisms or live-attenuated microorganisms. Disadvantages of such vaccine preparations include difficulty in large-scale production, safety considerations in handling and production, and the risks involved in immunizing elderly or immunodeficient individuals with live-attenuated vaccines.

Subunit vaccines, which utilize isolated components of a virus particle, have been developed as a safer alternative to conventional vaccines (Arnon). The components are typically recombinant proteins or synthetic short peptides. Influenza subunit vaccines, containing the surface proteins HA (haemagglutinin) and NA (neuraminidase), have proven to be less toxic than inactivated whole virus but of inferior protective capacity and immunogenicity (Engelhard, Potter). In particular, subunit vaccines have been ineffective in eliciting a CTL (cytotoxic T-lymphocyte) response (Arnon). The CTL response stimulates the production of T-lymphocytes, which attack cells perceived as abnormal, including virus-infected cells. Soluble subunit vaccines generally elicit only the humoral immune response, which stimulates B-lymphocytes to produce antibodies. Such a response is effective in attacking bacteria and viruses in the extracellular media, but not in the elimination of intracellular bacteria, parasites and virus-infected cells.

It is therefore desirable to provide an improved subunit influenza vaccine, which can elicit a strong humoral and CTL immune response without adverse side effects. In addition to producing an immediate immune response, an ideal vaccine should also provide a long-lived protective effect without the need for frequent booster doses.

SUMMARY OF THE INVENTION

The invention provides, in one aspect, a liposomal vaccine composition for use in immunizing a mammalian subject against influenza virus. The vaccine is composed of a suspension of liposomes, which encapsulate an influenza subunit antigen, and at least one immunostimulating cytokine. The antigen is effective to stimulate an immune response in the subject, and the cytokine or cytokines are effective to enhance the immune response. Preferably, the vaccine is effective to produce 100% seroconversion in such a subject for up to six months, and more preferably for up to nine months or more, after administration.

In one embodiment, the antigen and the cytokine or cytokines are coencapsulated in the same liposomes in the composition. Alternatively, they may be encapsulated in different populations of liposomes in the composition.

The influenza subunit antigen contains the HA (haemagglutinin) and NA (neuraminidase) viral surface proteins of an influenza virus, or antigenic mutants of these proteins. The cytokine is preferably selected from the group consisting of IL-1, IL-2, IL-4, IL-6, IL-7, IL-12, IL-15, IFN-$\gamma$, and GM-CSF. Preferred cytokines are interleukin-2 (IL-2), granulocyte macrophage colony stimulating factor (GM-CSF), or a combination of the two.

In one embodiment of the liposomal composition, the liposomes include at least 70 mole percent dimyristoyl phosphatidylcholine (DMPC). A composition used for intraperitoneal, subcutaneous or intramuscular administration preferably contains liposomes in the form of large multilamellar vesicles (MLV's) having a mean diameter of approximately 0.25$\mu$ to 5.0$\mu$. For use in intravenous, intranasal, or intramuscular administration, the liposomes are preferably small unilamellar vesicles (SUV's) having a mean diameter of approximately 30 to 80 nm. The SUV's may contain 1–25 mole percent of a lipid having a polar head group, typically a phosphate containing head group, derivatized with a polyethylene glycol (PEG) chain which has a molecular weight of between 750 and 10,000 daltons.

Also provided is a liposomal vaccine composition containing an influenza subunit antigen and at least one immunostimulating cytokine as provided above, where at least one of these components is encapsulated within a liposomal suspension, and where the resulting composition is effective to produce 100% seroconversion in a mammalian subject for up to six months, and preferably for up to nine months or more, after administration. A particularly preferred composition of this type produces an anti-H antibody titer of at least 200, as measured by haemagglutination-inhibition (HI) assay, up to six months after administration.

In another aspect, the invention provides a method of preventing infection of a mammalian subject by influenza virus, comprising administering to the subject an effective amount of a liposomal vaccine composition. The composition contains a suspension of liposomes, which encapsulate an influenza subunit antigen and at least one immunostimulating cytokine, as described above. For use in a method of immunization via intravenous, intranasal or intramuscular administration, the liposomes are preferably small unilamellar vesicles (SUV's) having a mean diameter of approximately 30 to 80 nm. The SUV's may contain 1–25 mole percent of a lipid having a polar head group, typically a phosphate containing head group, derivatized with a polyethylene glycol (PEG) chain which has a molecular weight of between 750 and 10,000 daltons.

In a related embodiment of the method, there is administered an effective amount of a liposomal vaccine composition containing an influenza subunit antigen and at least one immunostimulating cytokine as provided above, where at least one of these components is encapsulated within a liposomal suspension, and where the resulting composition is effective to produce 100% seroconversion in a mammalian subject up to six months after administration.

DETAILED DESCRIPTION OF THE INVENTION

I. Definitions

Figure 1A:
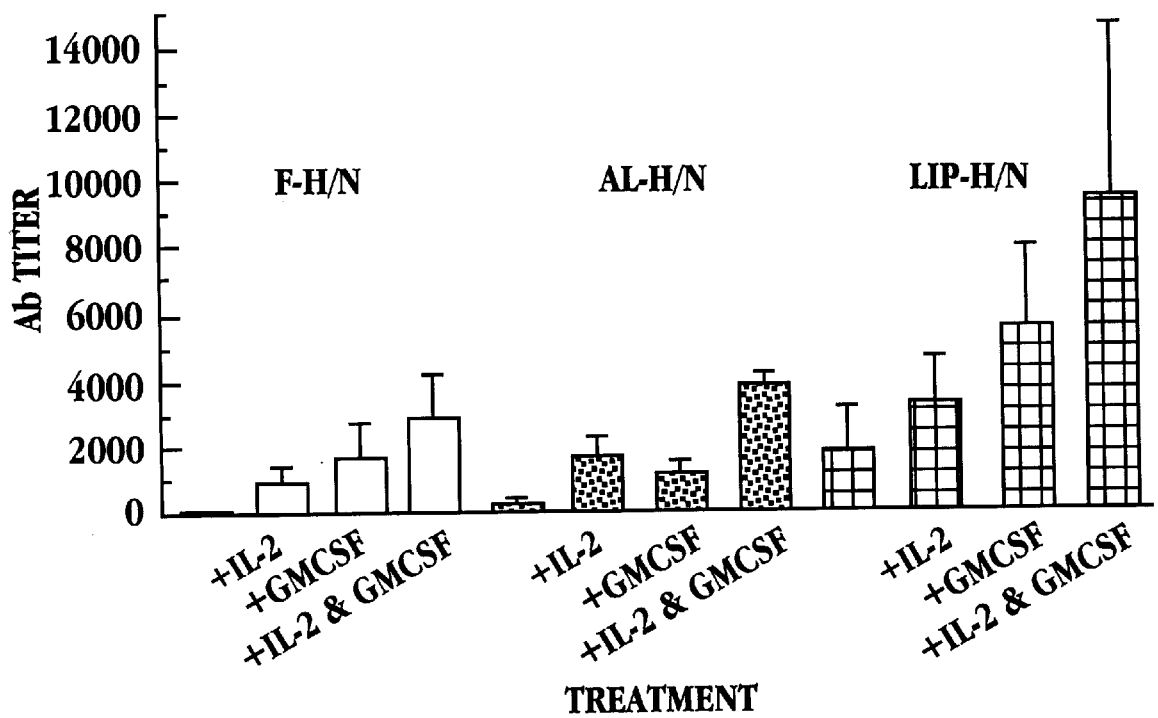
FIG. 1A shows levels of total serum antibodies measured by ELISA 40 days after i.p. immunization of BALB/c mice with 0.5 $\mu$g free H3N2 ("H/N") antigen, AL-H/N (H/N antigen with Alum adjuvant), and Lip-H/N (H/N antigen delivered in DMPC liposomes), each alone or in conjunction with 45000 CU of free IL-2, GM-CSF, or a combination of IL-2 and GM-CSF.

The terms below have the following meanings unless indicated otherwise. "Vesicle-forming lipids" refers to amphipathic lipids which have hydrophobic and polar head group moieties, and which (a) can form spontaneously into bilayer vesicles in water, as exemplified by phospholipids, or (b) are stably incorporated into lipid bilayers, with the hydrophobic moiety in contact with the interior, hydrophobic region of the bilayer membrane, and the polar head group moiety oriented toward the exterior, polar surface of the membrane.

The vesicle-forming lipids of this type typically include one or two hydrophobic acyl hydrocarbon chains or a steroid group and may contain a chemically reactive group, such as an amine, acid, ester, aldehyde or alcohol, at the polar head group. Included in this class are the phospholipids, such as phosphatidyl choline (PC), phosphatidyl ethanolamine (PE), phosphatidic acid (PA), phosphatidyl inositol (PI), and sphingomyelin (SM), where the two hydrocarbon chains are typically between about 14–22 carbon atoms in length, and have varying degrees of unsaturation. Other vesicle-forming lipids include glycolipids, such as cerebrosides and gangliosides, and sterols, such as cholesterol.

A "mutant" of an influenza virus, or of the viral surface proteins HA and/or NA, is an altered virus, or surface protein thereof, resulting from a heritable change, not induced through the incorporation of foreign DNA, in the genome of the virus. Such a change (mutation) results in a new strain that may elude protective immunity directed toward earlier strains. A "Cetus unit" (CU) is equal to six International Units (IU) of Immunological Activity, the international reference standard of a biological preparation of interleukin-2 (IL-2). The term "unit" used herein in reference to cytokine levels refers to Cetus units.

"Seroconversion" refers to the demonstration of specific antibody production in the serum of an individual who has been previously negative for that antibody. In the haemagglutination-inhibition (HI) assay (Shapira-Nahor) used herein for measuring specific anti-H antibodies, a titer of 40 or above, that is, where inhibition is seen at serum dilutions of 40× or greater, is considered evidence of seroconversion.

"Separately encapsulated", with reference to liposome-encapsulated agents, such as an antigen and a cytokine, indicates that a given vesicle or population or vesicles contains only one of such agents. "Co-encapsulated" indicates that a given vesicle or population of vesicles preferably contains a combination, or all, of such agents.

II. Liposomal Influenza Vaccine Compositions

The present invention is directed to influenza vaccines containing a subunit antigen and one or more immunostimulating cytokines. The cytokines are effective to enhance the immune response evoked by the antigen, specifically by enhancing antigen-presenting cell (APC) as well as B- and T-cell reactivity. At least one of the antigen and the cytokine, and preferably both components, are encapsulated in liposomes. Liposomes improve antigen delivery and processing, and provide sustained release of the cytokines at the site of administration. The components may be co-encapsulated or separately encapsulated, as defined above. Separately encapsulated compositions are generally preferred for the sake of convenience, and preliminary results indicates that their effectiveness is equal or superior to co-encapsulated vaccines.

Many strains of influenza virus are known, and antigenic drift (mutation) is common. The influenza virus particle is surrounded by a bilayer lipid envelope in which two virally coded glycoproteins, hemagglutinin (HA) and neuraminidase (NA), are embedded. A protein matrix (M) lies beneath, surrounding eight single stranded RNA molecules, nucleoprotein (NP) and 3 polymerases (P1–P3). Three viral types (A, B and C) are known according to antigenic differences in the NP and M proteins. The A viruses are further subdivided into subtypes based on variations in HA and NA. Common subtypes include those designated H1N1, H2N2, and H3N2. Frequent influenza outbreaks are due primarily to the considerable antigenic variation of the surface HA and NA glycoproteins, resulting in renewed susceptibility to infection. New subtypes could arise from point mutations (drift) in both A and B types, leading to minor antigenic changes occurring sequentially with time in HA and NA (Both). Antibodies produced in the humoral response to influenza subunit vaccines are highly strain specific and thus lose their protective effect when exposed to different or frequently mutating strains.

The composition and method of the invention are applicable to any of the various strains of influenza virus described above, i.e., the A, B, or C strains, subtypes within these strains, and mutants thereof. Included in the possible subunit antigens, for example, are all combinations of the two subunit proteins (haemagglutinin/neuraminidase, or H/N) such as H1N1, H2N2, and H3N2, and mutants thereof.

Cytokines useful for enhancing immune responses include IL-1, IL-2, IL-4, IL-6, IL-7, IL-12, IL-15, IFN-γ, and GM-CSF. Preferred cytokines for the present invention are GM-CSF (granulocyte macrophage colony stimulating factor), which acts as a growth and maturation factor for macrophages and dendritic cells (antigen presenting cells, or APC), and IL-2 (interleukin 2), which acts as a growth and maturation factor for T-lymphocytes.

A. Lipid Components

Various vesicle-forming lipids, as defined above, have been used for forming liposomal compositions, according to methods well known in the art. Preferred lipids for the current invention allow long-term storage of the liposome-entrapped antigen and cytokines and effective release of these components upon administration. Representative lipids include, but are not limited to, dimyristoyl phosphatidylcholine (DMPC), dimyristoyl phosphatidylglycerol (DMPG), cholesterol, egg phosphatidylcholine (egg PC), phosphatidyl ethanolamine (PE), phosphatidyl inositol (PI), 1,2-distearoyl-3-trimethylammonium propane (DSTAP), 1,2-dimyristoyl-3-trimethylammonium propane (DMTAP), and combinations thereof, such as DMPC/cholesterol, DMPC/DMPG, DMPC/DSTAP, and DMPG/DMTAP. Preferred compositions contain 10–100 mole percent DMPC. Particularly preferred compositions include 9:1 (mol/mol) DMPC/DMPG and 100% DMPC.

The liposomes may be large multilamellar vesicles (MLV), as described below, having a mean diameter of approximately 0.25$\mu$ to 5.0$\mu$. Alternatively, they may be small unilamellar vesicles (SUV) having a mean diameter of approximately 30–80 nm. In the latter case, the vesicle-forming lipids making up the liposomes may contain 1–25 mole percent of a lipid having a polar head group, typically a phosphate containing head group, derivatized with a polyethylene glycol (PEG) chain which has a molecular weight of between 750 and 10,000 daltons.

The preparation of such lipids is described in e.g. Woodle. The PEG chain may be linked directly to the phosphatidic acid head group of a phospholipid. Various other linkages are possible; for example, lipids containing a phosphatidyl ethanolamine (PE) or other amino head group may be conveniently coupled to activated PEG chains via reaction with brominated PEG. Woodle describes other methods of coupling a lipid amine (specifically PE) with PEG, including activation of hydroxy-terminated PEG with a carbonyl diimidazole coupling reagent, followed by reaction with the lipid amine to form a carbamate linkage. PEG end-capped with a carboxyl group may be reacted with a lipid amine to form an amide linkage (Sears).

Liposomes prepared from such lipids are known to have long circulating times in vivo (Woodle). Because such liposomes are not rapidly taken up by the RES, they may be used effectively for delivery of the vaccine components (antigen and cytokine) to dendritic cells, thus enhancing the CTL immune response, as discussed above.

B. Preparation of Liposomes and Liposomal Compositions

The following sections describe methods of preparing liposomal suspensions in accordance with the invention, and methods of incorporating additional components into the liposomes.

Liposomes may be prepared by a variety of techniques, such as those detailed in Szoka et al. To form multilamellar vesicles (MLV's), a mixture of vesicle-forming lipids dissolved in a suitable solvent is evaporated in a vessel to form a thin film, which is then hydrated by an aqueous medium to form MLV's, typically with sizes between about 0.1 to 10 microns. Tertbutanol is a preferred solvent for the process, and MLV's prepared using this solvent are termed TB-MLV's. The MLV's may then be downsized to a desired size range of 1.0 microns or less by extruding aqueous suspension through a polycarbonate membrane having a selected uniform pore size, typically 0.05 to 1.0 microns.

Preparations of MLV's or REV's (described below) may be treated, e.g. by extrusion, sonication or homogenization, to produce small unilamellar vesicles (SUV's), which are characterized by sizes in the 0.03–0.08 micron range. Alternatively, SUV's may be formed directly by homogenization of an aqueous dispersion of lipids.

Various methods are available for encapsulating other agents in liposomes. For example, in the reverse phase evaporation method (Szoka, U.S. Pat. No. 4,235,871) a nonaqueous solution of vesicle-forming lipids is dispersed with a smaller volume of an aqueous medium to form a water-in-oil emulsion. The agent to be incorporated is included either in the lipid solution, in the case of a lipophilic agent, or in the aqueous medium, in the case of a water-soluble agent. After removal of the lipid solvent, the resulting gel is converted to liposomes. These reverse phase evaporation vesicles (REVs) have typical average sizes between about 2–4 microns and are predominantly oligolamellar, that is, containing one or a few lipid bilayer shells. The REVs may be sized by extrusion, if desired, to give oligolamellar vesicles having a maximum selected size between about 0.05 to 1.5 microns.

Other methods for adding additional components to liposomal compositions are illustrated in the Examples below. In Example 1, an aqueous liposome dispersion is colyophilized with other components and the resulting solid redispersed to form MLV's. Example 2 illustrates a method (Adler) in which an aqueous solution of the agent to be encapsulated is added to a t-butanol solution of lipids. The mixture is sonicated and lyophilized, and the resulting powder is rehydrated.

Liposome compositions containing an entrapped agent may be treated after final sizing, if necessary, to remove free (non-entrapped) agent. Conventional separation techniques, such as centrifugation, diafiltration, and molecular-sieve chromatography are suitable for this purpose. The composition may also be sterilized by filtration through a conventional 0.45 micron depth filter.

To form the compositions of the current invention, the concentration of antigen and/or cytokine in the liposomes is preferably effective to give a protein/lipid molar ratio between about 1:100 and 1:1000.

C. Encapsulation Efficiency and Storage Stability of the Liposomal Compositions

For compositions prepared as described in Examples 1–4, the efficiency of encapsulation was 95%, 92% and 40% for the antigen, IL-2 and GM-CSF, respectively (see Example 6). Upon storage at 4° C., the liposome carrier was fully stable at 1 year, and the entrapped agents retained 75–95% of their initial activity for at least 3–6 months, with IL-2 liposomes being particularly stable. The IL-2 and antigen liposomes showed less than 10% loss of activity for up to 6 months.

Stabilizers may also be added to the liposomal compositions. For example, when a metal chelator such as Desferal™ or diethylenetriamine pentaacetic acid (DTPA) was included in the lyophilization medium at a concentration of 100 $\mu$M, the IL-2 biological activity loss was reduced further. Preservatives such as BHT (see Example 2) or Vitamin E (see Example 3) may also be included.

For longer term storage, the compositions may be stored as the dry lyophilized powder, which is stable for at least a year, and hydrated to form an aqueous suspension before use.

The two cytokines, IL-2 and GM-CSF, may also be incorporated into the same vesicles (see Example 5). In this case, the encapsulation efficiency was 85% and 40%, respectively.

D. Administration

For use in humans, a preferred antigen dose is in the range of 1 to 20 $\mu$g. Parenteral administration may be by injection, e.g., intraperitoneal (ip), subcutaneous (sc), intravenous (iv), or intramuscular (im). For iv or im administration, the liposomes of the composition are preferably small unilamellar liposomes, as described above (Sections IIA and IIB), and more preferably contain 1–25 mole percent of PEG-derivatized lipid, also described above (Section IIA). The vaccine may also be administered intranasally, via the mucosal membrane.

III. Immunogenic Activity of the Liposomal Vaccines A. Compositions and Methods

For the tests described below, influenza A virus haemagglutinin/neuraminidase (designated "H/N" or "HN" in the Figures and discussion) and the cytokines GM-CSF and IL-2 were encapsulated, each separately, in large (mean diameter, 1.5$\mu$) multilamellar vesicles (MLV) composed of dimyristoyl phosphatidylcholine (DMPC), as described in Examples 1–4 below.

For the results shown in FIGS. 1, 6, 7 and 9 and Table I below, a commercial 1993 preparation of influenza A virus (Shandong H3N2), provided by Sulvay Duphar B. V., the Netherlands, designated antigen 1, was used. For the results shown in FIGS. 2–5 and 8 and Tables II–V, a 1994 preparation from the Swiss Serum and Vaccine Institute, Berne, Switzerland, designated antigen 2, was used.

For measurement of the humoral response after immunization, BALB/C mice were injected once intraperitoneally (i.p.) or subcutaneously (s.c.), using the compositions described below. The total antigen per injection was in the range of 0.15 to 2.0 $\mu$g, with 0.5 $\mu$g being a typical dose. Serum antibodies were tested at different intervals (11–360 days after vaccination), using the haemagglutination-inhibition (HI) assay for specific anti-H antibodies (Shapira-Nahor), enzyme (neuramidinase, or NA) neutralization for specific anti-N antibodies, and ELISA (Ben-Ahmeida, 1993) for total anti-H/N antibodies. Control experiments demonstrated that empty MLV liposomes produced no measurable response in the HI assay.

In the ELISA and NA tests, the last serum dilution yielding 50% maximum inhibition of absorption, respectively, was determined. All groups consisted of 5–6 mice each. In the HI test, a titer (i.e., maximum serum dilution showing inhibition) of 40 or greater is considered evidence of seroconversion; i.e., protection against viral infection.

To evaluate long-term protection against viral infection, ten or fourteen months after vaccination, mice were infected by intranasal administration of live virus (2000 haemagglutinin units). Animals were sacrificed after six days for lung examination. In mice infected with the virus, multiple necrotic foci were evident. Full (100%) protection was recorded when the lungs were totally free of foci.

B. Humoral Response and Long Term Protection: Free, Alum-Supported and Liposomal Antigen with and without Free Cytokines In the first series of tests (Example 7 below), the humoral immune response of mice immunized with nonencapsulated (free) and encapsulated (liposomal) antigens, with and without additional treatment with free cytokines (IL-2 and/or GM-CSF), was measured. BALB/c mice were immunized once, i.p., with 0.5 $\mu$g F-H/N (antigen 1, free), AL-H/N (alum-supported), or Lip-H/N (liposomal, prepared as described in Example 1 below). Each antigen was tested alone and in conjunction with 45000 units IL-2, GM-CSF, or a combination of IL-2/GM-CSF.

ELISA antibody titers measured 40 days post-vaccination are shown in FIG. 1A. The mean antibody titer of mice vaccinated with Lip-H/N, without cytokines, was 7 and 20 times higher than that of mice immunized with AL-H/N and with F-H/N, respectively. Co-injection of each of the above antigens together with either GM-CSF or IL-2 (nonencapsulated) augmented the response further (5- to 20-fold). This pattern was also found at later stages of the response, 150–240 days post vaccination (data not shown).

Figure 1B:
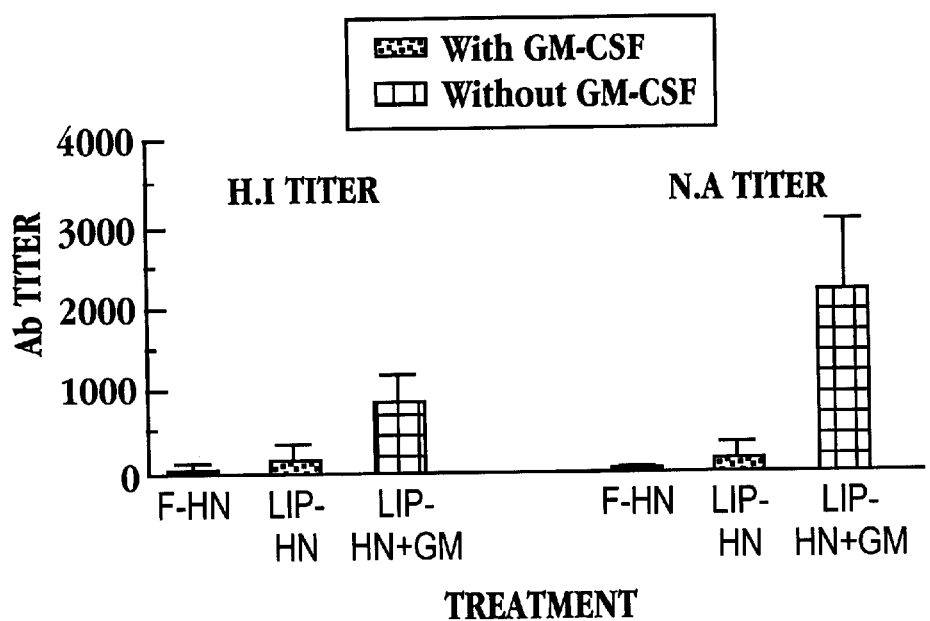
FIG. 1B shows levels of anti-H antibodies as measured by HI (haemagglutination-inhibition) assay and anti-NA antibodies as measured by enzyme neutralization, 40 days after i.p. immunization of BALB/c mice with 0.5 $\mu$g free H/N or Lip-H/N (H/N antigen delivered in DMPC liposomes), each alone or in conjunction with 45000 CU GM-CSF, as in FIG. 1A.

Anti-H (HI) and anti-N (NA) antibody response of similar compositions were also tested 40 days postvaccination, giving the results shown in FIG. 1B. As can be seen from the figure, liposome encapsulation of the antigen increased the titer, in both cases, to approximately 200, and addition of GM-CSF further increased the HI titer by approximately threefold and the NA titer by approximately tenfold. Because the NA surface protein is less variable from one influenza virus strain to another than the HI protein, a composition giving a strong anti-NA immune response is likely to provide broad protection against a wide range of such viruses.

Table I shows long term protection demonstrated in BALB/c mice when administered live influenza virus 10 months after immunization with the compositions described above. Protection was evidenced by the absence of necrotic foci six days after administration. Liposomal antigens and compositions incorporating cytokines, particular IL-2, showed high levels of protection, with 100% protection being typical for compositions having both of these features.

The level of serum conversion (i.e. HI titer of 40 or greater), up to 8 months after vaccination, is given in Table II. Liposomal antigen preparations (antigen 2) showed the highest levels of seroconversion at both early (day 11) and late stages (day 240). In particular, liposomal antigen plus GM-CSF produced 100% seroconversion at all stages of testing.

TABLE I

Long Term Protection (%) 10 Months Post-Vaccination

| | Cytokine | | | |
|---|---|---|---|---|
| Antigen | None | IL-2 | GM-CSF | IL-2 + GM-CSF |
| Free H/N | 20 | 100 | 40 | 66 |
| Al-H/N | 25 | 100 | 100 | 100 |
| Lip-H/N | 25 | 100 | 400 | 80 |

TABLE II

Serum Conversion (Titre ≥ 40) Following Vaccination of Balb/C Mice with Non-Liposomal and Liposomal Influence A H/N Vaccines

| | % of Mice Seroconverted* | | | |
|---|---|---|---|---|
| Vaccine | Day 11 | Day 45 | Day 70 | Day 240 |
| F-HN | 0 | 40 | 40 | 40 |
| F-HN + IL-2 | 40 | 80 | 80 | 75 |
| F-HN + GM-CSF | 60 | 80 | 80 | 60 |
| F-HN + IL-2 + GM-CSF | 40 | 100 | 100 | 100 |
| Al-HN | 20 | 100 | 80 | 40 |
| Al-HN + IL-2 | 40 | 100 | 75 | 60 |
| Al-HN + GM-CSF | 40 | 100 | 100 | 80 |
| Al-HN + IL-2 + GM-CSF | 60 | 100 | 100 | 100 |
| Lip-HN | 60 | 100 | 100 | 100 |
| Lip-HN + IL-2 | 40 | 100 | 75 | 67 |
| Lip-HN + GM-CSF | 100 | 100 | 100 | 100 |
| Lip-HN + IL-2 + GM-CSF | 100 | 100 | 100 | 100 |

*4–6 mice/group

Figure 2A:
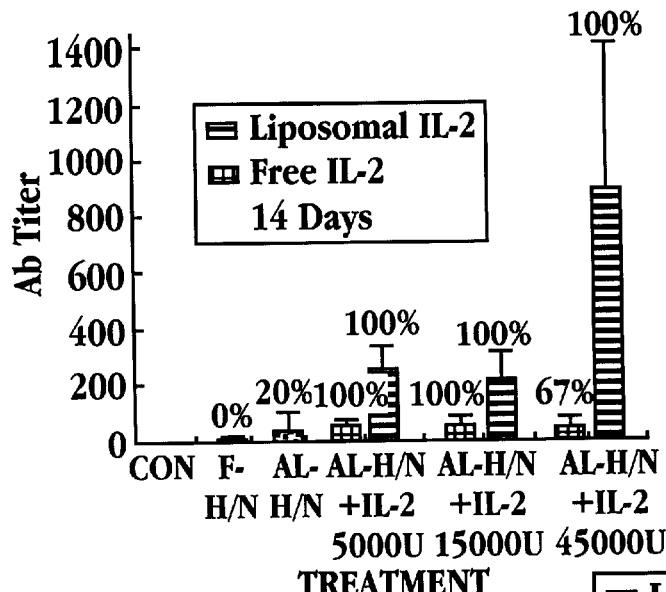
FIGS. 2A–2C show levels of anti-H antibodies measured 14 days, 45 days, and 167 days after i.p. immunization of BALB/c mice with 0.5 $\mu$g free H/N or AL-H/N (H/N antigen with Alum adjuvant), the latter alone or in conjunction with three dosages of free IL-2 or Lip-IL-2 (IL-2 encapsulated in liposomes)
Figure 2B:
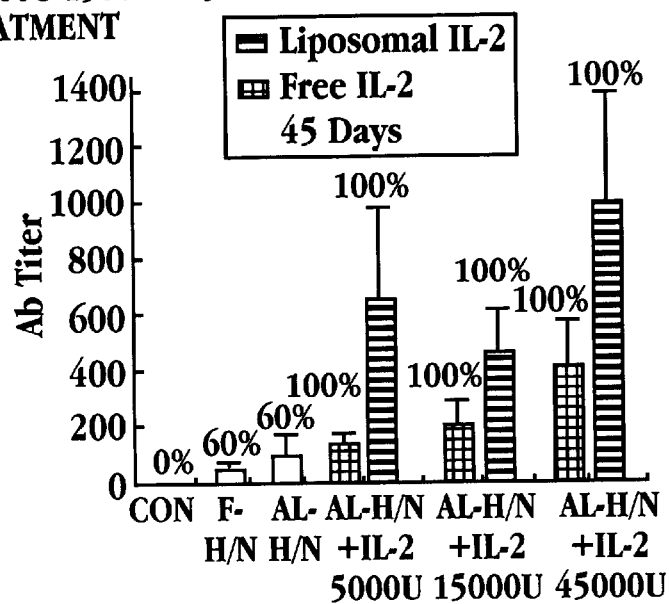
Figure 2C:
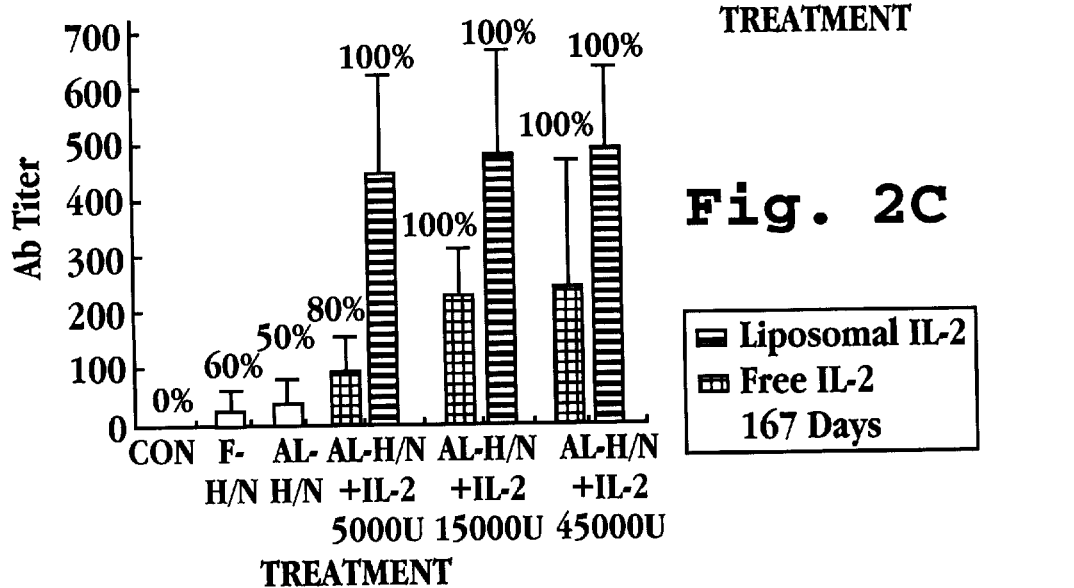

C. Humoral Response: Free and Alum-Supported Antigen with and without Free and Liposomal Cytokines In this series of tests (Example 8), mice were immunized once, i.p., with 0.5 μg H/N (antigen 2), free (F-H/N) or Alum-adsorbed (AL-H/N). Additional groups were vaccinated with AL-H/N combined with $5 \times 10^3$, $15 \times 10^3$ or $45 \times 10^3$ U (Cetus units) of free or liposome-encapsulated IL-2, prepared as described in Example 2 below. The response was measured by HI (FIGS. 2A–2C) and by ELISA (FIGS. 3A–3B) at 14, 45, and 167 days. In FIGS. 2A–2C, the numbers above the bars indicate the percent seroconversion (minimum titer 40) among the group of animals tested.

As can be seen in FIGS. 2A–2C, only a weak HI response was evident in mice immunized with AL-H/N alone. Addition of free IL-2 elicited a low response at 14 days and a moderate response, at the higher doses, at 45 and 167 days. A marked and persistent increase in anti-H antibody titer (at least tenfold at 167 days at all dosages of IL-2) was demonstrated in mice given AL-H/N together with liposomal IL-2.

Figure 3A:
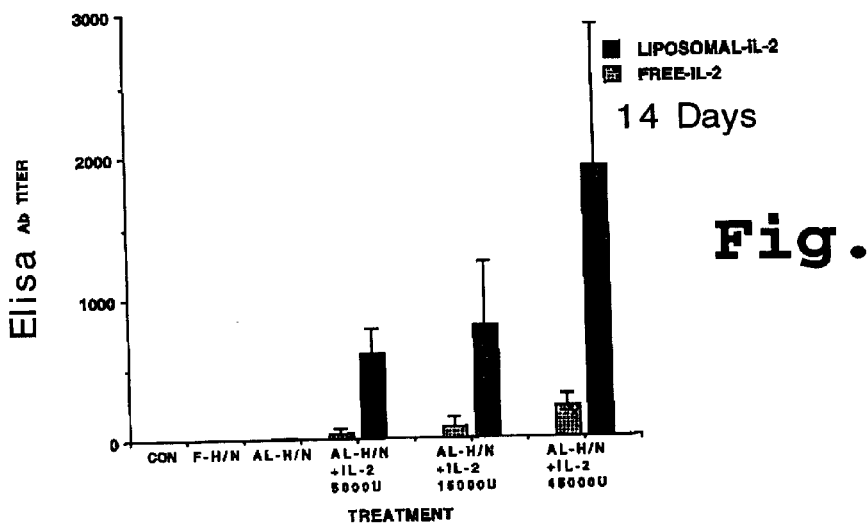
FIGS. 3A–3C show levels of total serum antibodies measured by ELISA 14 days, 45 days and 167 days after i.p. immunization of BALB/c mice with the compositions described for FIGS. 2A–2C.
Figure 3B:
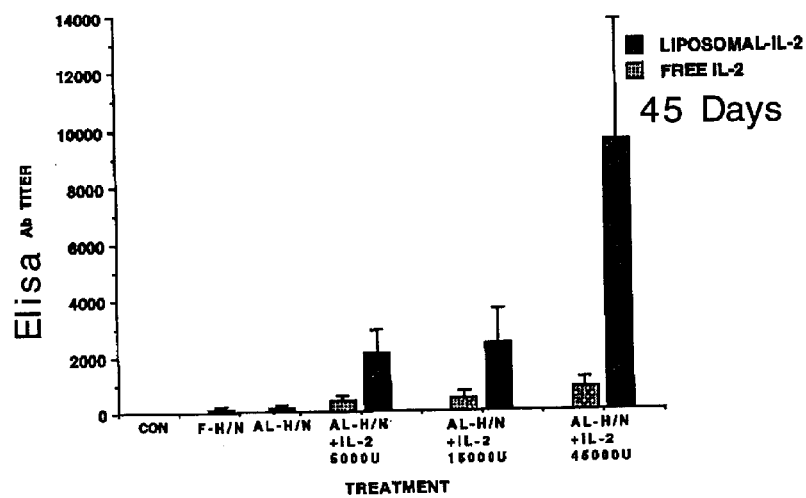
Figure 3C:
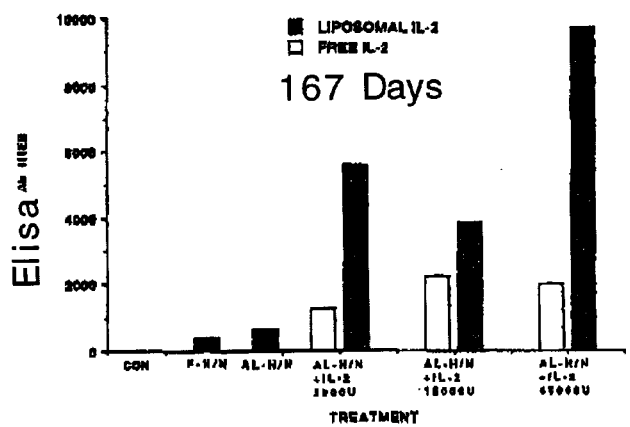
Figure 4A:
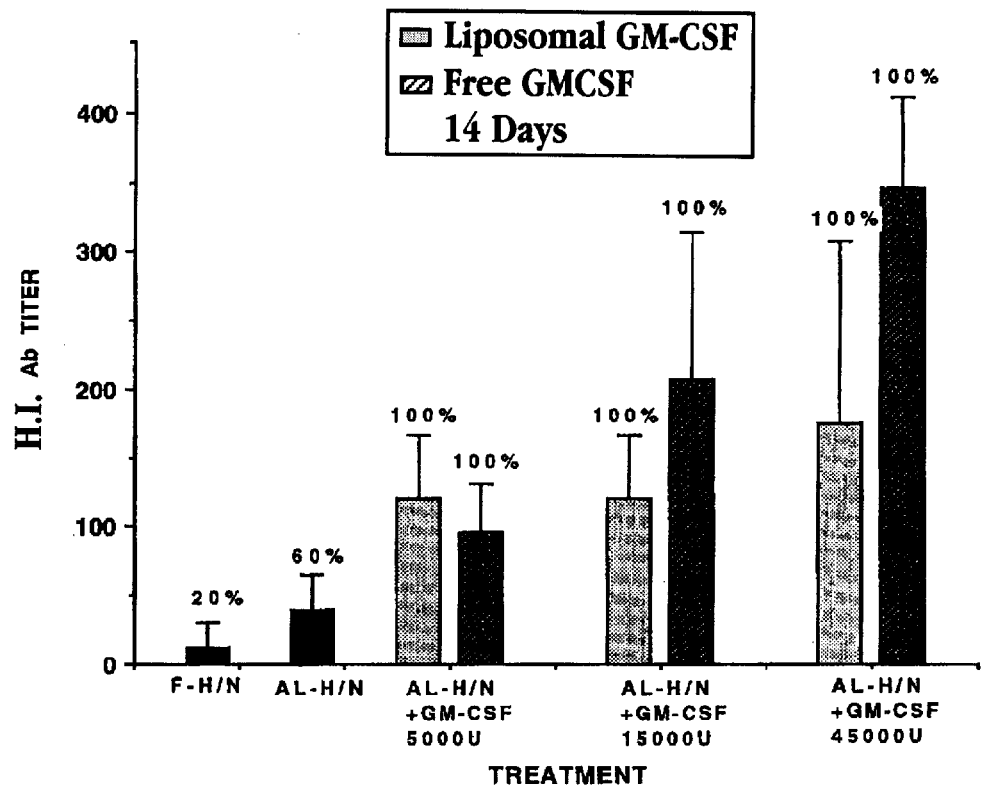
FIGS. 4A–4D show levels of anti-H antibodies measured 14 days, 45 days, 173 days and 276 days (9 months) after i.p. immunization of BALB/c mice with 0.5 $\mu$g free H/N or AL-H/N, the latter alone or in conjunction with three dosages of free GM-CSF or Lip-GM-CSF (GM-CSF encapsulated in liposomes)
Figure 4B:
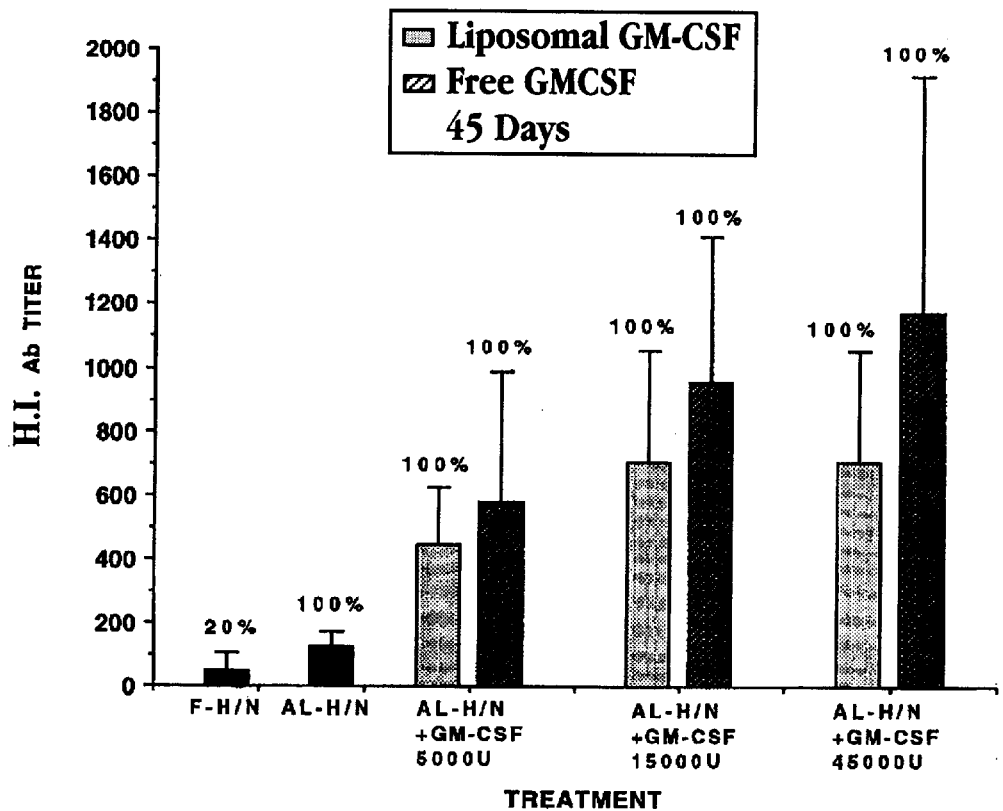
Figure 4C:
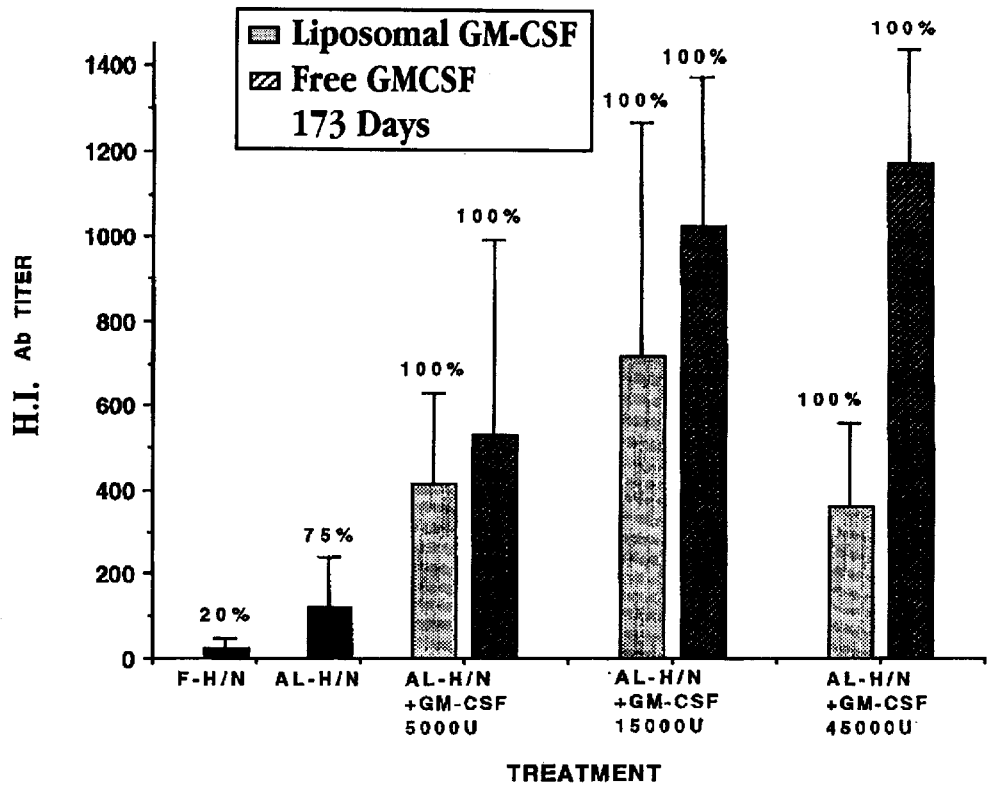
Figure 4D:
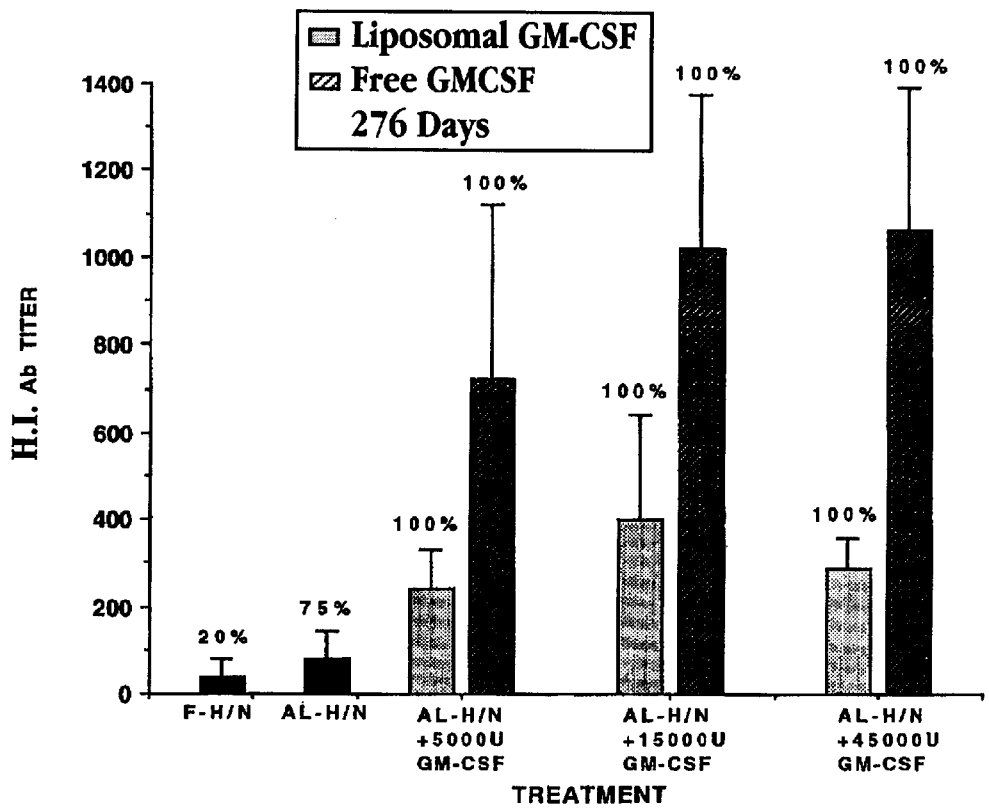
Figure 5A:
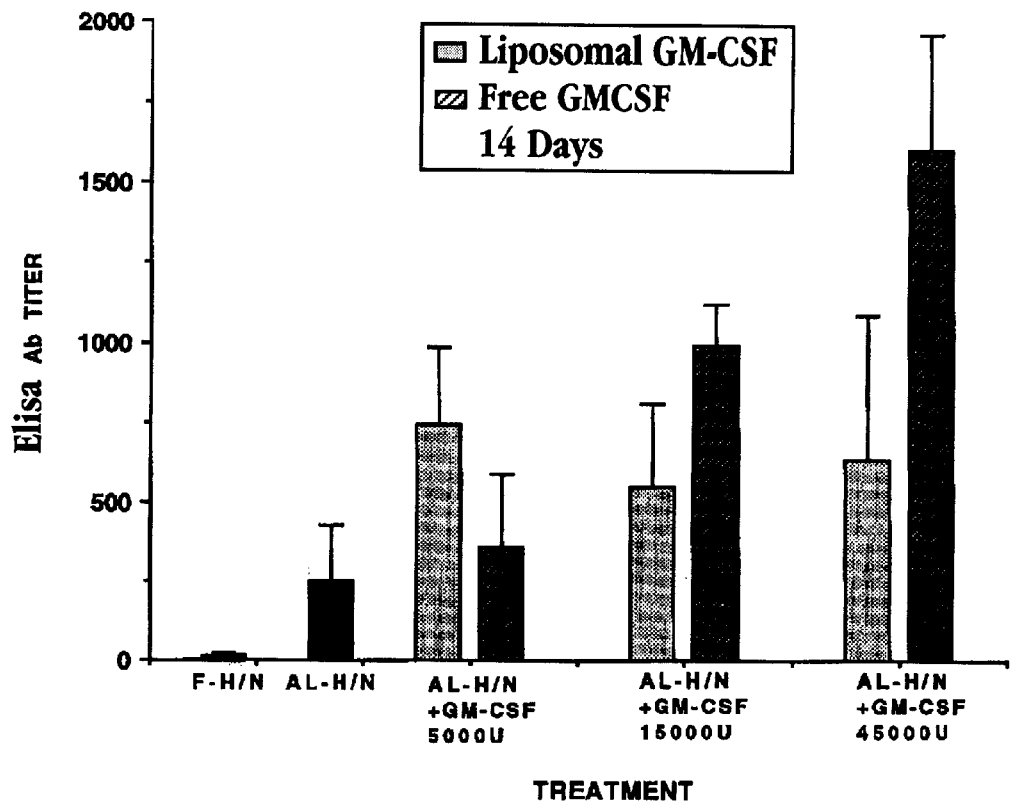
FIGS. 5A–5D show levels of total serum antibodies measured 14 days, 45 days, 173 days and 276 days (9 months) after i.p. immunization of BALB/c mice with 0.5 $\mu$g free H/N or AL-H/N, the latter alone or in conjunction with three dosages of free GM-CSF or Lip-GM-CSF.
Figure 5B:
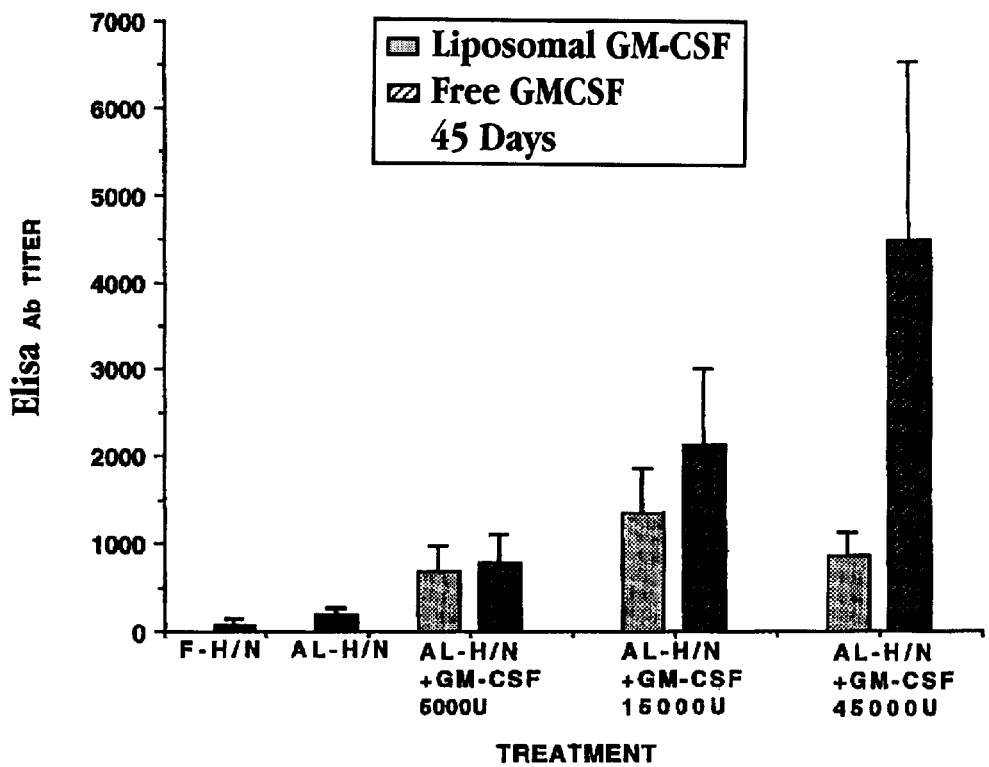
Figure 5C:
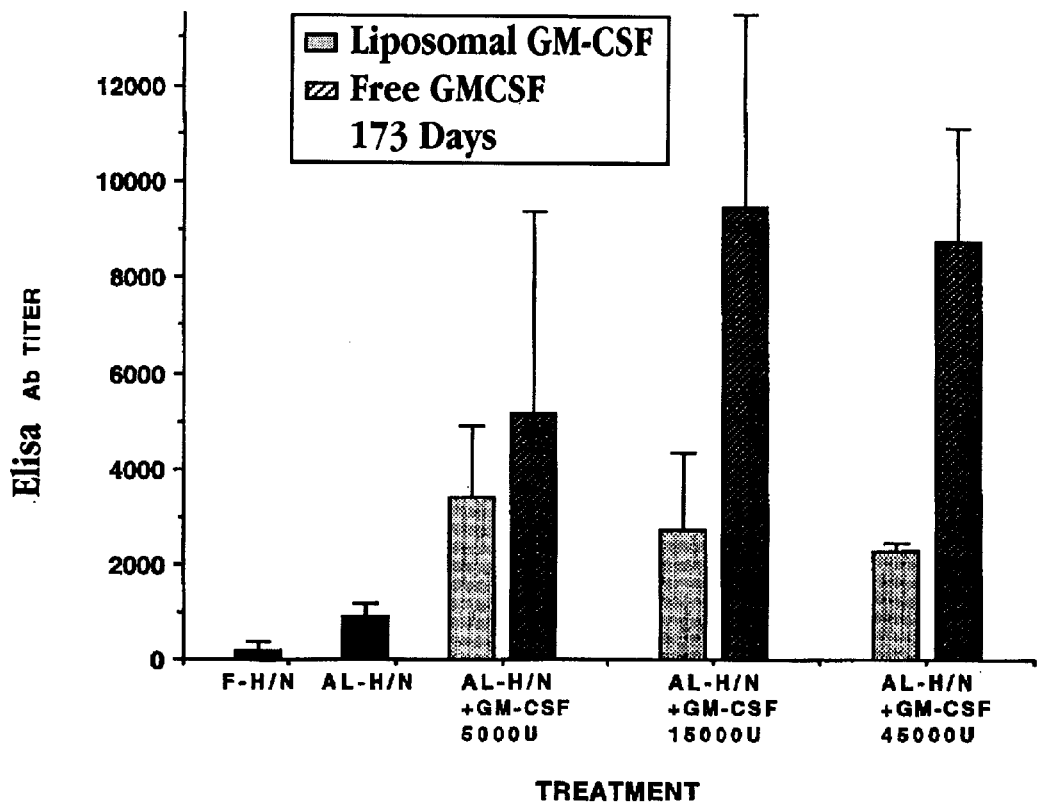
Figure 5D:
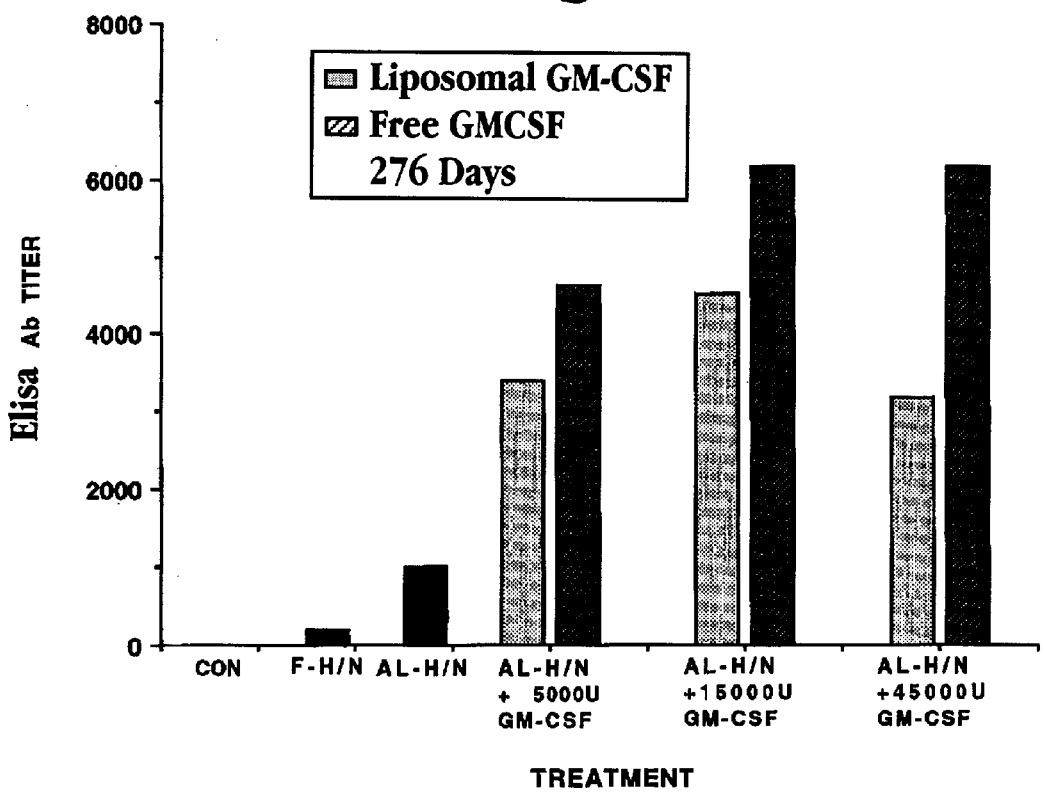
Figure 6:
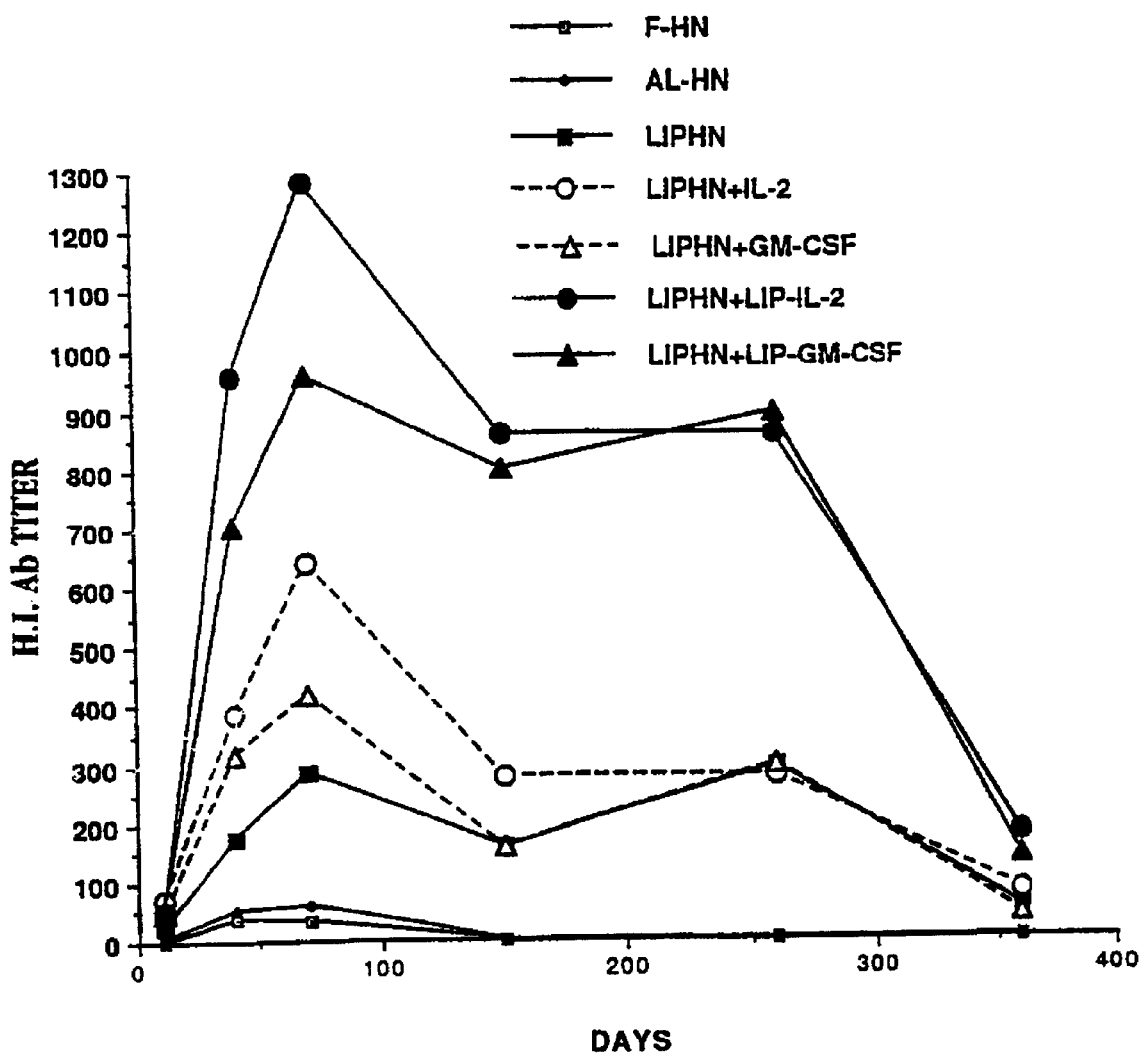
FIG. 6 shows levels of anti-H serum antibodies measured 11, 40, 70, 150, 270 and 360 days after i.p. immunization of BALB/c mice with 0.5 $\mu$g free H/N, AL-H/N, and Lip-H/N, the last alone or in combination with 45000 C.U. IL-2, Lip-IL-2, GM-CSF, or Lip-GM-CSF.

All compositions containing liposomal IL-2 showed 100% seroconversion at all stages, with H.I. titers typically 200 or more, and 400 or more at later stages. Similar results were shown by ELISA assay of total antibodies, with higher doses showing a greater response (FIGS. 3A–3C).

This series of tests was repeated, using GM-CSF in place of IL-2, to give the results shown in FIGS. 4A–4D (anti-H titer) and FIGS. 5A–5D (total antibody titer). In FIGS. 4A–4D, the numbers above the bars indicate the percent seroconversion among the group of animals tested. Again, addition of the cytokine, particularly when entrapped in liposomes, produced a significant increase in antibody titer. All liposomal cytokine compositions produced 100% seroconversion at all stages up to 9 months, with H.I. titers as high as 1000, and total antibody titers of 4000–8000, observed at later stages.

D. Humoral Response and Long Term Protection: Free and Liposomal Antigen with and without Free and Liposomal Cytokines Mice were immunized once, i.p., with 0.5 μg H/N (antigen 1), free, Alum-adsorbed, or liposome-encapsulated. The Lip-H/N was administered alone or co-administered with free IL-2, free GM-CSF, liposomal IL-2, or liposomal GM-CSF (45000 C.U.; prepared as described in Examples 1–2 below). Mice were tested on days 11–360 for anti-H antibody response, to give the results shown in FIG. 6.

As can be seen in the Figure, mice vaccinated with F-H/N or AL-H/N alone exhibited a low and relatively short-lived HI titer, lasting approximately 3 months. A much higher titer, lasting 1 year, was seen in mice injected with Lip-H/N.

Co-administration of non-encapsulated IL-2 or GM-CSF modestly enhanced the response to Lip-H/N during 3–5 months post vaccination. In comparison, co-administration of Lip-IL-2 or Lip-GM-CSF (combined liposomal vaccine) significantly augmented the response to Lip-H/N throughout the observation period (360 days). After 3 months, for example, the titers obtained for the combined vaccines (solid circle and triangle) were greater than twice those observed for those in which only the antigen was encapsulated (open circle and triangle). At 5 and 9 months, a greater than threefold difference was seen. After one year, the combined vaccines still showed H.I. titers of approximately 150–200.

Figure 7A:
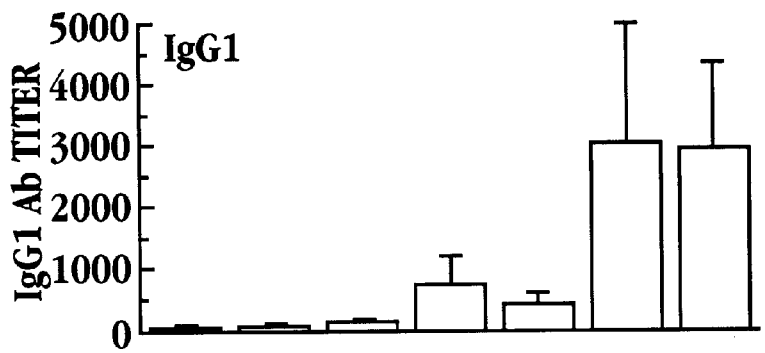
FIGS. 7A, 7B, and 7C show levels of specific antibody subtypes IgG1, IgG2a, and IgG3, respectively, measured by ELISA 70 days after i.p immunization of BALB/c mice with the compositions described for FIG. 6.
Figure 7B:
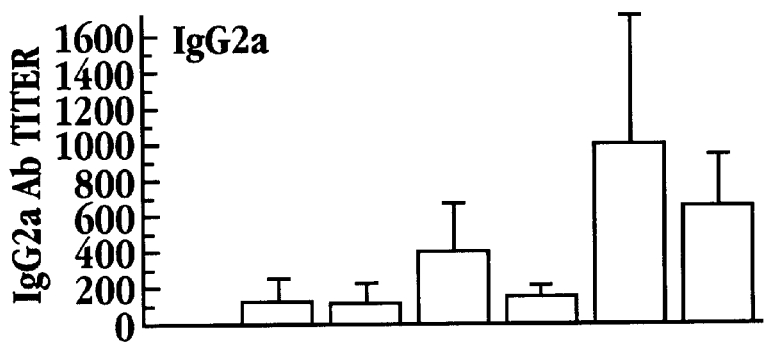
Figure 7C:
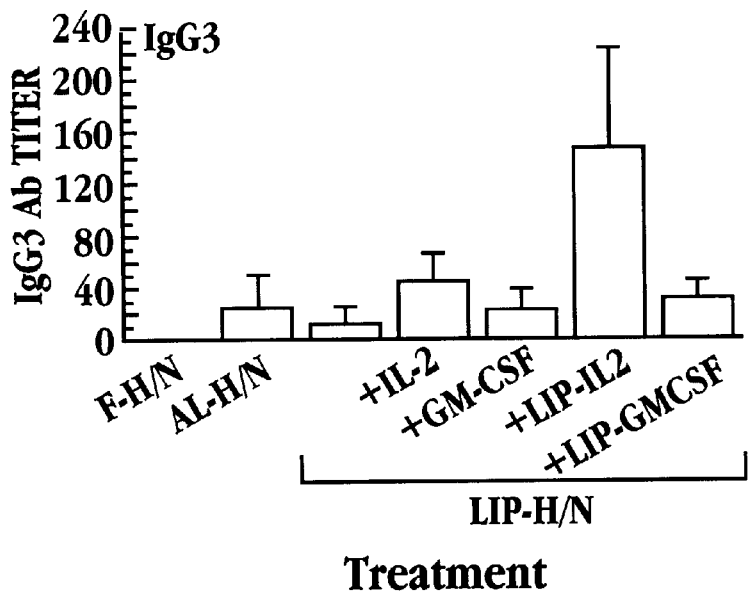

Further analysis of the antibody response revealed that mice vaccinated with Lip-H/N+Lip-IL-2 or Lip-GM-CSF also developed a much higher titer of IgG1, IgG2a and IgG3 antibodies than mice immunized with the non-liposomal vaccines (FIGS. 7A–7C). These observations suggest that the liposomal vaccines trigger both Th1 and Th2 (helper T-cell) responses. Again, the combined liposomal vaccines typically gave titers severalfold higher than the other vaccine compositions.

The level of serum conversion (i.e. HI titer of 40 or more) of mice vaccinated as described above with various dosage forms of antigen, where liposomal antigen was combined with free and liposomal cytokines, is shown in Table III. As shown in the table, the combined liposomal vaccines (Lip-HN+Lip-cytokine) showed 100% seroconversion from the early stage (11 days) up to one year after vaccination.

TABLE III

Serum Conversion (Titre ≥ 40) Following Vaccination of Balb/C Mice with Non-Liposomal and Liposomal Influenza A H/N Vaccines

| | % of Mice Seroconverted* | | | | | |
|---|---|---|---|---|---|---|
| Vaccine | Day 11 | Day 45 | Day 70 | Day 180 | Day 240 | Day 360 |
| F-HN | 0 | 40 | 50 | 0 | 0 | 0 |
| AL-HN | 0 | 75 | 80 | 0 | 0 | 0 |
| Lip-HN | 20 | 100 | 100 | 100 | 100 | 33 |
| Lip-HN + IL-2 | 100 | 100 | 100 | 100 | 100 | 100 |
| Lip-HN + GM-CSF | 100 | 100 | 100 | 100 | 80 | 40 |
| Lip-HN + Lip-IL-2 | 100 | 100 | 100 | 100 | 100 | 100 |
| Lip-HN + Lip-GM-CSF | 100 | 100 | 100 | 100 | 100 | 100 |

*4–6 mice/group

Figure 8:
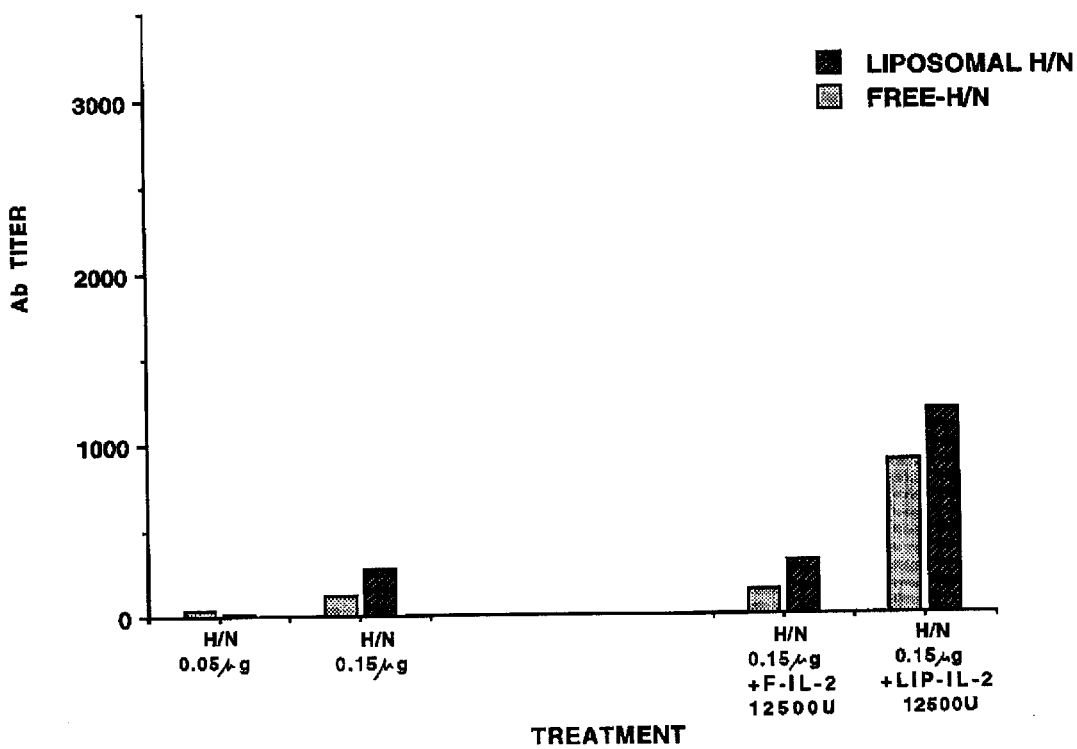
FIG. 8 shows total antibody levels as measured by ELISA after i.p. injection of BALB/c mice with 0.15 $\mu$g free and liposomal H/N, with and without free and liposomal IL-2.

FIG. 8 shows total antibody response, as measured by ELISA, 45 days after administration of free and liposomal H/N (antigen 2), alone or with free or liposomal IL-2. Addition of free IL-2 to a low (0.15 μg) dosage of antigen had little effect on the response, but addition of liposomal IL-2 increased the response significantly.

Figure 9:
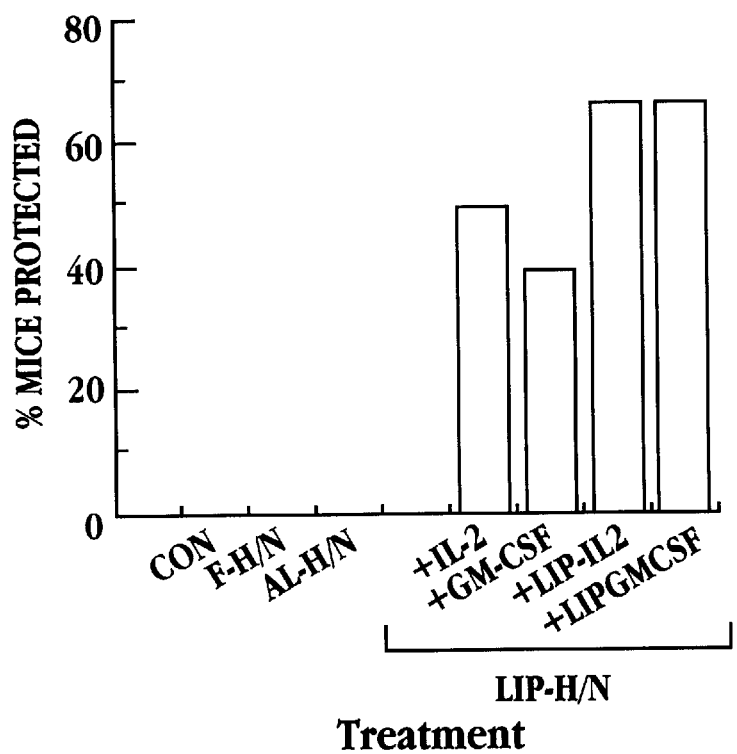
FIG. 9 shows long term protection in BALB/c mice when administered live influenza virus intranasally 14 months after immunization, i.p. or s.c., with the compositions described for FIG. 6.

Finally, mice were tested for long-term protection 14 months after vaccination (FIG. 9). The level of protection upon co-vaccination with Lip-H/N (antigen 2)+liposomal cytokines was 70% at 14 months, as compared with 40–50% in mice immunized with Lip-H/N+free cytokines, and no protection in mice immunized with free, liposomal or AL-H/N without cytokines. Thus, a single immunization with the combined liposomal vaccine afforded a high level of protection for over 1 year.

E. Cytotoxic Response: Liposomal Antigen with Liposomal Cytokines

A strong anti-viral cytotoxic response was found in mice immunized with the combined liposomal vaccine (liposomal H/N+liposomal IL-2 or GM-CSF). To obtain the data shown in Table IV, BALB/C mice were immunized s.c. at 0 and 90 days with 0.5 μg H/N with or without $5 \times 10^4$ U cytokine, in the combinations shown. Splenocytes obtained on day 18 after the second vaccination were stimulated in vitro at a 1:1 ratio with influenza virus-infected irradiated syngeneic splenocytes for 5 days. Cytotoxicity was measured by the 4 hour $^{51}$Cr release assay (Gazit) against virus infected P815 cells. Cytotoxicity is expressed in terms of LU/$10^6$ cells, where 1 LU corresponds to 30% cytotoxicity.

As shown in Table IV, the cells from mice immunized with the combination liposomal vaccine exhibited a strong cytotoxic activity against the virus-infected target cells, *with an increased activity at a higher E/T (electors to target cell) ratio.

TABLE IV

Cytotoxic Activity of Balb/C Spleen Cells Following Vaccination with Influenza A H/N Vaccines[a]

| Vaccine | Cytotoxicity (LU/$10^6$ Cells) Against:[b] | |
| --- | --- | --- |
|  | Non-Infected P815 | Infected P815 |
| F-HN (0.5 μg) | <1 | <1 |
| Al-HN | <1 | <1 |
| Lip-HN | <1 | <1 |
| Lip-HN + Lip-GM-CSF ($5 \times 10^4$ U) | 9.4 | 32.5 |
| Lip-HN + Lip-IL-2 ($5 \times 10^4$ U) | 4.8 | 19.1 |

[a]Spleen cells obtained 90 days after s.c. immunization were co-cultured for 5 days with virus-infected syngeneic splenocytes prior to testing.
[b]Cytotoxicity was tested against virus infected and non-infected target cells at various effector/target cell ratios, using a 4 hr $^{51}$Cr release assay. 1 LU = 30% toxicity.

To obtain the data shown in Table V, mice were immunized as described above with the vaccine compositions shown. Splenocytes obtained 90 days after immunization were co-cultured for 5 days with influenza virus-infected irradiated syngeneic splenocytes prior to testing. Cytotoxicity was tested against both virus-infected and non-infected P815 target cells, again by the 4 hour $^{51}$Cr release assay. As shown in Table V, cells from mice immunized with combination vaccines (H/N plus cytokine) showed significant cytotoxicity, with greater activity demonstrated against the virus-infected cells.

TABLE V

Cytotoxic Activity of Splenocytes from Mice Immunized with Nonliposomal and Liposomal H/N

| Vaccine[a] | % Cytotoxicity at E/T Ratio of[b] | |
| --- | --- | --- |
|  | 10:1 | 40:1 |
| F-HN | 1 | 10 |
| Al-HN | 1 | 5 |
| Lip-HN + Lip-IL-2 | 21 | 40 |
| Lip-NH + Lip-GM-CSF | 29 | 50 |

[a]Balb/C mice were immunized s.c. on days 0 and 90 with 0.5 μg HN ± cytokines ($5 \times 10^4$ U).
[b]Splenocytes obtained on day 18 after the second vaccination were stimulated in vitro at 1:1 ratio with virus-infected irradiated syngeneic splenocytes for 5 days. Cytotoxicity was measured by the 4 hour $^{51}$Cr release assay against virus infected P815 target cells.

The results described above show that liposomal encapsulation of antigens and either IL-2 or GM-CSF appreciably improves the immune response, including the CTL response, to subunit vaccines. Co-administration of liposomal antigen and liposomal IL-2 or GM-CSF (combined liposomal vaccine) elicited a high titer of IgG1, IgG2a, IgG3 and IgM antibodies, indicating both Th1 and Th2 responses, as well as strong CTL responses, and were the most effective in long-term protection experiments. The combined liposomal vaccine induces an earlier response, a stronger response, and a more extended response as compared with currently available influenza vaccines and the comparative vaccines tested.

The following examples illustrate but are not intended in any way to limit the invention.

Materials and Methods

A. Antigens

Commercial preparations of influenza A virus haemagglutinin/neuraminidase were provided by Sulvay Duphar B. V., the Netherlands (Shandong [9/93] H3N2), and by the Swiss Serum and Vaccine Institute, Berne, Switzerland.

B. Cytokines

Recombinant mouse granulocyte/macrophage colony-stimulating factor (GM-CSF, >97% pure, $4 \times 10^7$ U/mg) and recombinant human interleukin-2 (IL-2, 97% pure, $3 \times 10^6$ Cetus units/mg=$18 \times 10^6$ IU/mg) were provided by Immunex (Seattle, Wash., USA) and Cetus Oncology (Chiron, Emeryville, Calif., USA), respectively. The cytokines were handled according to the suppliers' instructions and diluted in Hank's Balanced Salt Solution (HBSS) containing 1 mg/ml bovine serum albumin (BSA).

C. Mice

Specific pathogen-free (SPF) female BALB/c mice (Harlan, Jerusalem), aged 6–12 weeks, were maintained under SPF conditions.

D. Cytokine Bioassays

The ability of free and liposome-entrapped cytokines to induce proliferation was assessed by a 48 [3H]-thymidine incorporation test (Gillis) or by the colorimetric MTT test (Mossmann). The GM-CSF-dependent 32-D mouse myeloid cell line and the IL-2-dependent CTLL-2 mouse T-cell line were used as indicator cells. For testing liposome-encapsulated cytokines in the MTT assay, 20% Triton x-100 in O.1N HCl was used to dissolve the color crystals and the liposomes and to prevent turbidity related artifacts.

E. Preparation of Alum-Adsorbed Antigens

The H/N proteins were adsorbed onto Alum, $Al(OH)_3$, as previously described (Harlow), using 100 μg H/N per 1 mg $Al(OH)_3$.

F. Immunization and Measurement of Humoral Response

BALB/C mice were injected once intraperitoneally (ip), unless otherwise indicated, with H/N, typically at a 0.5 μg dosage level, administered either as free antigen (F-H/N), combined with Alum (AL-H/N), or in liposomes (Lip-H/N) (prepared as in Example 1, below). Each of the antigen preparations was given either alone or together with $5 \times 10^2 – 4.5 \times 10^4$ Cetus units (CU) of free or liposome-encapsulated cytokines (prepared as in Examples 2–3).

Serum antibodies were tested at different intervals (11–360 days after vaccination), using the haemagglutination-inhibition (HI) assay for specific anti-H antibodies (Shapira-Nahor), enzyme neutralization for specific anti-N antibodies, and ELISA (Ben-Ahmeida, 1993) for total anti-H/N antibodies. In the HI test, a titer of 40 or greater is considered to be protective. In the anti-N and ELISA tests, the last serum dilution yielding 50% maximum inhibition or absorption, respectively, was determined. All groups consisted of 5–6 mice each.

G. Protection Against Viral Infection

Ten or fourteen months post vaccination, mice were infected by intranasal administration of live virus (2000 haemagglutination units). Since this virus strain is rarely lethal to BALB/C mice, animals were sacrificed on day 6 for lung examination. In mice infected with the virus, multiple necrotic foci were evident. Full protection was recorded when the lungs were totally free of foci.

H. Statistical Analysis

Differences between groups were analyzed using the two-tailed Student's t-test.

EXAMPLE 1

Preparation of Liposomal H/N

The antigen was entrapped in DMPC liposomes using the dehydration-rehydration technique, as follows. Dimyristoyl phosphatidylcholine (DMPC, Avanti Polar Lipids, Pelham, Ala., USA, or Lipoid, Ludwigshafen, Germany), 4 g, was added to 40 ml sterile double distilled water (DDW) and dissolved at 40–45° C. The solution was homogenized for 3 min. at high pressure (10,000 psi), using the Rannie Minilab 8.30 H High Pressure Homogenizer (APV Rannie, Denmark), resulting in the formation of small unilamellar vesicles (50 nm, SUV). The SUV were sterilized by filtration through a 0.2 μm pore size filter. H/N (66 μg in 0.2 ml) was added to 750 μl of the SUV (lipid/protein ratio 1000/1), and the mixture was vortexed briefly and then co-lyophilized overnight. The lipid-protein powder was hydrated by adding first 0.1 ml DDW and then 0.65 ml phosphate buffered saline (PBS) at pH 7.4, followed by vortexing, resulting in the formation of large (mean diameter, 1.5 μm) multilamellar vesicles (MLV) containing H/N.

The amount of protein entrapped in the liposomes was determined by the filter paper dye-binding assay, using Coomassie brilliant blue G (Minamide).

EXAMPLE 2

Preparation of Liposomal Cytokines

DMPC (0.57 g) and 0.02 ml of 1% solution of BHT (butylated hydroxytoluene, an antioxidant) in methanol were mixed with 9 ml tertiary butanol, and the mixture was sonicated at 37° C. for 20 min to dissolve the lipid. Subsequently, GM-CSF or IL-2 ($1$–$5\times10^6$ U in 9 ml HBSS+ 0.1% BSA) was added, and the lipid-cytokine mixture was further sonicated for 20 min at room temperature and lyophilized overnight. The powder was hydrated by adding 9 ml DDW and immediately shaking (Labline Multi Wrist Shaker, Melrose Park, Ill., USA) for 30 min at room temperature. The above GM-CSF-loaded liposomes and IL-2-loaded liposomes (mean diameter, 1.5±0.5 μm) were diluted in HBSS/0.1% BSA and stored at 4° C. Liposomes containing cytokines were separated from the free, nonencapsulated cytokines by centrifugation (Eppendorf centrifuge model 5415C) at 14,000 rpm for 15–20 min. This technique resulted in almost 100% recovery of the liposomal lipids in the liposome fraction.

To measure encapsulation efficiency, the liposomes were first separated from the medium as described above. The level of biologically active cytokines was then determined in the original preparation, in the liposome-free medium and in the isolated liposomes by bioassays, described above. For maximum exposure (>95%) of the liposomal cytokines, the liposomes were sonicated for 30–40 min at 4–8° C. This procedure resulted in excellent recovery of cytokine, with >90% retention of the cytokine biologic activity.

EXAMPLE 3

Liposomal cytokines were prepared as described in Example 2, except that BHT was replaced by 0.1–0.2 mole % (relative to DMPC) of Vitamin E.

EXAMPLE 4

Liposomal cytokines were prepared as in Example 2, with the addition of a metal chelator such as DTPA (diethylenetriamine pentaacetic acid) or Desferal at a level of ≧50 μM (final concentration), to prevent transition of metal-related damage to the protein.

EXAMPLE 5

MLV were prepared as described in Example 1 except that H/N proteins and cytokines (IL-2, GM-CSF, or a combination of the two) were co-lyophilized together with DMPC.

EXAMPLE 6

Encapsulation of Antigens and Cytokines in Liposomes and Stability of the Liposomal Preparations The influenza A H3N2 antigens and the recombinant cytokines IL-2 and GM-CSF were encapsulated in large MLV (mean diameter, 1.5 μm) consisting of DMPC. The encapsulation efficiency was tested by measuring proteins (H3N2) and cytokine biologic activity (GM-CSF, IL-2) in the supernatants and the liposome fraction following centrifugation, as described above. The mean encapsulation efficiency of the antigens, IL-2 and GM-CSF (3 batches each) was 95%, 92% and 40%, respectively.

In addition, the liposomes were stored in liquid form at 4° C. for 2 to 8 months, during which time the preparations were tested periodically for residual activity, as compared with the fresh preparations. The encapsulated IL-2 and H3N2 were stored up to 6 and 8 months, respectively, without any significant loss of activity (<10%). The encapsulated GM-CSF showed a 10–25% decrease in activity at 2 months, with a further decrease (40–50%) at 5 months. Thus, the liposomal IL-2 preparation is by far more stable than the liposomal GM-CSF. The loss of GM-CSF activity was partly due to cytokine leakage from the liposomes and partly to cytokine inactivation/degradation.

In other experiments (data not shown), both IL-2 and GM-CSF were incorporated into the same vesicles. In this case, the encapsulation efficiency was ~85% and 40%, respectively. No stability studies were carried out with these liposomes.

Following i.v. inoculation of the liposomal cytokines, the blood circulation time was 10–20 times longer than that of the non-encapsulated cytokines (data not shown).

EXAMPLE 7.

Humoral Immune Response of Mice Immunized with Free or Liposomal H/N, with and without Co-administration of Free Cytokines BALB/c mice were immunized once, ip, with 0.5 μg F-H/N, AL-H/N, or Lip-H/N (prepared as in Example 1), each alone or in conjunction with free IL-2, GM-CSF, or IL-2+GM-CSF ($4.5 \times 10^4$ units each). The antibody titer was measured by ELISA and HI (for specific anti-H antibodies) on days 11–240. Lung protection was tested, as described above, on day 270 post vaccination. The results are shown in FIGS. 1–2, as discussed above.

EXAMPLE 8

Effect of Free and Liposomal IL-2 on the Humoral Immune Response to Alum-Adsorbed H/N Mice were immunized once, ip, with 0.5 μg H/N, free or Alum-adsorbed. Other groups were vaccinated with AL-H/N combined with $5 \times 10^3$, $15 \times 10^3$ or $45 \times 10^3$ Cetus units of free or encapsulated IL-2 or GM-CSF, prepared as described in Example 2. The response was measured by HI and ELISA tests on days 14, 45, 167, and (for GM-CSF) 276 (9 months). The results are shown in FIGS. 2–5, as discussed above.

EXAMPLE 9

Humoral Immune Response of Mice Immunized with Free or Liposomal H/N, with and without Co-Administration of Free or Liposomal Cytokines A comparison was made between soluble and liposome-entrapped IL-2 and GM-CSF co-administered with Lip-H/N. Mice were tested on days 11–360 for anti-H antibody response, to give the results shown in FIG. 6.

Further analysis of the antibody response was carried out to measure the titer of IgG1, IgG2a and IgG3 antibodies. Results are shown in FIGS. 8A–8C.

Mice were tested on day 420 for long-term protection, as described above, to give the results shown in FIG. 9.

EXAMPLE 10

Cytotoxic Response

A strong anti-viral cytotoxic response was found in mice immunized with the combined liposomal vaccines (Lip-H/N+Lip-IL-2 or Lip-GM-CSF). Thus, splenocytes of mice vaccinated 3 months previously that were stimulated in vitro for 6 days with influenza A-infected syngeneic splenocytes, exhibited a strong cytotoxic activity against virus-infected target cells (P815). Results are shown in Tables IV and V above.

While the invention has been described with reference to specific methods and embodiments, it will be appreciated that various modifications may be made without departing from the invention.

It is claimed:

1. A liposomal vaccine composition for use in immunizing a mammalian subject against influenza virus, comprising a suspension of liposomes, having encapsulated therein
   an influenza subunit antigen effective to stimulate an immune response in the subject, and
   at least one immunostimulating cytokine effective to enhance the immune response.

2. The composition of claim 1, wherein the antigen and the cytokine are coencapsulated in the same liposomes in the composition.

3. The composition of claim 1, wherein the antigen and the cytokine are encapsulated in different populations of liposomes in the composition.

4. The composition of claim 1, where the influenza subunit antigen comprises the HA (haemagglutinin) and NA (neuraminidase) viral surface proteins of an influenza virus, or antigenic mutants thereof.

5. The composition of claim 1, where the cytokine is selected from the group consisting of IL-1, IL-2, IL-4, IL-6, IL-7, IL-12, IL-15, IFN-γ, and GM-CSF.

6. The composition of claim 5, where the cytokine is interleukin-2 (IL-2).

7. The composition of claim 5, where the cytokine is granulocyte macrophage colony stimulating factor (GM-CSF).

8. The composition of claim 5, where the cytokine is a combination of IL-2 and GM-CSF.

9. The composition of claim 1, where the liposomes comprise at least 70 mole percent dimyristoyl phosphatidyl-choline (DMPC).

10. The composition of claim 1, for use in intraperitoneal, intramuscular or subcutaneous administration, wherein the liposomes are large multilamellar vesicles having a mean diameter of approximately 0.25μ to 5.0μ.

11. The composition of claim 1, for use in intravenous, intranasal or intramuscular administration, wherein the liposomes are small unilamellar vesicles having a mean diameter of approximately 30 to 80 nm.

12. The composition of claim 11, wherein the liposomes contain 1–25 mole percent of a lipid having a polar head group derivatized with a polyethylene glycol (PEG) chain which has a molecular weight of between 750 and 10,000 daltons.

13. The composition of claim 1, wherein said composition is effective to produce 100% seroconversion in said subject up to six months after administration.

14. The composition of claim 13, wherein said composition is effective to produce 100% seroconversion in said subject up to nine months after administration.

15. A liposomal vaccine composition for use in immunizing a mammalian subject against influenza virus, comprising
   an influenza subunit antigen effective to stimulate an immune response in the subject, and
   at least one immunostimulating cytokine effective to enhance the immune response,
   wherein at least one of said antigen and cytokine is encapsulated within a liposomal suspension, and said composition is effective to produce 100% seroconversion in said subject up to six months after administration.

16. The composition of claim 15, wherein said composition is effective to produce 100% seroconversion in said subject up to nine months after administration.

17. A method of preventing infection of a mammalian subject by influenza virus, comprising administering to the subject an effective amount of a liposomal vaccine composition comprising a suspension of liposomes, having encapsulated therein an influenza subunit antigen effective to stimulate an immune response in the subject, and at least one immunostimulating cytokine effective to enhance the immune response.

18. The method of claim 17, for use in intravenous, intranasal or intramuscular administration, wherein the liposomes are small unilamellar vesicles having a mean diameter of approximately 30 to 80 nm.

19. The method of claim 18, for use in intravenous, intranasal or intramuscular administration, wherein the liposomes contain 1–25 mole percent of a lipid having a polar head group derivatized with a polyethylene glycol (PEG) chain which has a molecular weight of between 750 and 10,000 daltons.

20. A method of preventing infection of a mammalian subject by influenza virus, comprising administering to the subject an effective amount of a liposomal vaccine composition comprising an influenza subunit antigen effective to stimulate an immune response in the subject, and at least one immunostimulating cytokine effective to enhance the immune response, wherein at least one of said antigen and cytokine is encapsulated within a liposomal suspension, and said composition is effective to produce 100% seroconversion in said subject up to six months after administration.

* * * * *